United States Patent [19]
Nguyen et al.

[11] Patent Number: 6,110,476
[45] Date of Patent: Aug. 29, 2000

[54] SYSTEM FOR STABILIZING ASCORBIC ACID BASED ON A PHOSPHONIC ACID DERIVATIVE AND ON A METABISULFITE

[75] Inventors: Quang Lan Nguyen, Antony; Isabelle Afriat, Paris; Dang-Man Pham, Puteaux; Florence Chanvin, Soisy/S/Seine, all of France

[73] Assignee: L'Oreal, Paris, France

[21] Appl. No.: 09/145,454

[22] Filed: Sep. 2, 1998

[30] Foreign Application Priority Data

Sep. 2, 1997 [FR] France .................................. 97 10903

[51] Int. Cl.$^7$ ....................................................... A61K 7/00
[52] U.S. Cl. .......................... 424/401; 514/844; 514/846; 514/847; 514/848; 514/970; 514/973
[58] Field of Search ............................. 424/401; 514/844, 514/846, 847, 848, 970, 973

[56] References Cited

U.S. PATENT DOCUMENTS 5,552,446   9/1996   Candau et al. ........................ 514/772.4

FOREIGN PATENT DOCUMENTS 0 670 157 A1   9/1995   France .

OTHER PUBLICATIONS

WPIDS DNC C89–139186, Hara et al., JP 01233277 A, Sep. 19, 1989 (abstract).
Database WPI, Week 9440, Derwent Publications Ltd., London, GB; AN 94–322095; XP002067095 and JP 06 247 855 A (Wako Pure Chem Ind), Sep. 6, 1994 (Abstract).
Database WPI, Week 8914, Derwent Publications Ltd., London, GB; AN 89–102027; XP002067096 & HU 46 540 A (Hoffmann L.), Nov. 28, 1988 (Abstract).

*Primary Examiner*—Dwayne C. Jones
*Assistant Examiner*—C. Delacroix-Muirheid
*Attorney, Agent, or Firm*—Oblon, Spivak, McClelland, Maier & Neustadt, P.C.

[57] ABSTRACT

A synegistic system based on a phosphonic acid derivative and on a metabisulphite, for stabilizing ascorbic acid. The invention also relates to compositions, in particular cosmetic and dermatological compositions, containing ascorbic acid and this stabilizing system, and to the use of these compositions in the cosmetics and/or dermatological fields.

20 Claims, No Drawings

SYSTEM FOR STABILIZING ASCORBIC ACID BASED ON A PHOSPHONIC ACID DERIVATIVE AND ON A METABISULFITE

BACKGROUND OF THE INVENTION

1. Field of the Invention

The invention relates to a system based on a phosphonic acid derivative and on a metabisulphite, for stabilizing ascorbic acid, to the use of this system in compositions containing ascorbic acid, and to compositions containing it in particular in the cosmetics and/or dermatological fields.

The invention also relates to the use of the compositions obtained for the cosmetic treatment of human skin, as well as for the preparation of a cream or ointment intended for the dermatological treatment of human skin. These compositions can be applied topically, to the face, including the area around the eyes, to the body and to the scalp of human beings.

2. Discussion of the Background

It has been sought for a long time to stabilize ascorbic acid, or vitamin C, in appropriate pharmaceutical presentations, on account of its beneficial properties.

Ascorbic acid has many biological functions, such as the stimulation of collagen synthesis, the strengthening of skin tissues against external attacking factors (UV radiation, pollution), depigmentation, its anti-free-radical activity, and the compensation for vitamin E deficiency. Some of these beneficial properties have been reported in particular by England and Seifter in the article "The biochemical functions of ascorbic acid" published in Ann. Rev. Nutri., 1986, vol. 6, p. 365–406.

However, on account of its chemical structure (a-keto lactone), ascorbic acid is very sensitive to the influence of environmental parameters such as light, oxygen and water (due to its pH and due to the presence of traces of metals). This results in an unavoidable degradation over time of ascorbic acid in solution form. This degradation is reflected by a colour change and by the generation of carbon dioxide.

This problem has been approached in many ways in the prior art.

To reduce or delay the degradation of ascorbic acid in solution form, it has been recommended in document U.S. Pat. No. 5,140,043 to stabilize by introducing it into aqueous-alcohol solutions, formed of at least 80% water and having a pH of less than 3.5. On account of the strong acidity of these solutions, it is difficult to envisage them being used in the cosmetics and/or pharmaceutical field, since repeated application of these solutions can disrupt the skin's equilibrium and in particular irritate the skin or even burn it. In addition, at acidic pH, although the colour change is stabilized, the generation of carbon dioxide ($CO_2$) is not.

The article by B. R. Hajratwala entitled "Stability of ascorbic acid" published in the Revue Sciences Pharmaceutiques on Mar. 15, 1985 is moreover known. That article teaches in particular stabilizing ascorbic acid in aqueous acidic solution by adding a surfactant which is an oxyethylenated sorbitan ester. In particular, the author reported therein that at pH 3.4 and at 25° C., adding this agent decreased the rate of oxidation, and thus the rate of degradation of the ascorbic acid in solution. In addition, that document teaches the use of a chelating agent such as ethylene-diaminetetraacetic acid (EDTA), and conditioning under nitrogen in the absence of light, in order to improve the stability of ascorbic acid in aqueous solution. Such an aqueous acidic solution, applied to the skin, has the same drawbacks as those described above for the aqueous-alcoholic acidic solutions. Furthermore, the stabilization obtained is still insufficient.

Other ways of stabilizing ascorbic acid have been envisaged, in particular by coating (technique described in document FR-A-1,600,826) or by granulating ascorbic acid (technique illustrated in document JP-A-53-127,819, for the agrifood sector). However, these techniques are expensive, on the one hand, and can adversely affect the ascorbic acid, on the other hand, for example during heating, and/or can lead to uncosmetic compositions, as is the case with granules.

It is moreover known, from document FR-A-1,489,249, to use metal salts of phosphorylated ascorbic acid, in particular magnesium ascorbyl phosphate, in cosmetic compositions. The latter compound has a level of activity close to that of ascorbic acid, from which it is derived, but it has certain drawbacks which render its use on the skin unlikely. In particular, since magnesium ascorbyl phosphate is only stable at basic pH (pH 8 to pH 9), it must be incorporated into a basic composition which may be irritant to the skin (which has a pH value of about 5.5).

In addition, document EP-A-670,157 describes an emulsion containing stabilized ascorbic acid. However, this is a specific pharmaceutical form (water-in-oil emulsion) and it is desirable to be able to stabilize ascorbic acid in compositions in very varied pharmaceutical forms.

Consequently, the set of proposals which have been made hitherto has not made it possible to solve the technical problems associated with the instability of ascorbic acid, in any pharmaceutical form for the cosmetics and/or dermatological fields and at a cost which is compatible with the industrial requirements.

There is thus a need for a composition which can be used in particular in the cosmetics and/or dermatological fields, containing stabilized ascorbic acid, in a free form, i.e. which has no additional group acting in particular as stabilizer, which causes no skin irritation when it is applied, which can be in any pharmaceutical form and which is stable both as regards the colour and as regards the evolution of $CO_2$.

The Applicant has now found a system based on a phosphonic derivative and on metabisulphite, which allows ascorbic acid to be stabilized. A considerable synergistic effect of the system according to the invention is observed.

Admittedly, it is known to use phosphonic acid derivatives in compositions containing vitamin C (see EP-A-670, 157 mentioned above). It is also known to stabilize vitamin C with metabisulphite (see JP-A-6-247,855). However, the synergism of the combination claimed had never been observed.

SUMMARY OF THE INVENTION

The object of the present invention is a system for stabilizing ascorbic acid, comprising at least one phosphonic acid derivative and at least one metabisulphite, the phosphonic acid derivative and the metabisulphite being in sufficient amounts to act in synergy.

Another object of the invention is a method of using the system defined above to stabilize ascorbic acid.

DETAILED DESCRIPTION OF THE PREFERRED EMBODIMENTS

The phosphonic acid derivatives which can be used in the invention can be chosen in particular from ethylenediaminetetra(methylenephosphonic acid), hexamethylenediaminetetra(methylenephosphonic acid), diethylenetriaminepenta(methylenephosphonic acid), and their salts and in particular their sodium salts, such as pentasodium ethylenediaminetetra(methylenephosphonic acid).

Advantageously, ethylenediaminetetra(methylenephosphonic acid) is used, in particular the product sold by the company Monsanto under the name Dequest 2041. The pentasodium salt of this acid, sold under the name Dequest 2046 by the company Monsanto, can also advantageously be used.

The phosphonic acid derivative must be, in a composition containing it, in a sufficient amount to ensure the intended result. It can be present in an amount ranging, for example, from 0.005 to 5%, and preferably from 0.05 to 1%, of the total weight of the composition.

The metabisulphite can be an alkali-metal, alkaline-earth metal or ammonium salt of anhydrosulphurous acid. Sodium or potassium metabisulphite is preferably used. The metabisulphite must be present, in a composition containing it, in a sufficient amount to achieve the intended result. This amount can range, for example, from 0.005 to 5%, and preferably from 0.05 to 1%, of the total weight of the composition.

The weight ratio between the metabisulphite and the phosphonic acid derivative can range from 1 to 1000 and preferably from 1 to 5.

The system according to the invention allows effective stabilization of ascorbic acid. The stability of the ascorbic acid is further improved when the composition containing it has an aqueous phase with a pH ranging from 5.5 to 7.5, and in particular a pH of 6.

In this case, good stability of the ascorbic acid is observed, both as regards the colour change and as regards the generation of carbon dioxide.

Thus, the subject of the invention is also a composition containing ascorbic acid, characterized in that it contains the system indicated above.

As indicated above, the composition according to the invention preferably contains from 0.005 to 5% by weight of phosphonic acid derivative relative to the total weight of the composition, and from 0.005 to 5% by weight of metabisulphite relative to the total weight of the composition.

The composition containing the system according to the invention more particularly constitutes a composition for topical application, in particular a cosmetic and/or dermatological composition, and contains a physiologically acceptable medium, i.e. one which is compatible with the skin, the scalp and/or the hair.

Ascorbic acid is present in the composition according to the invention in an appropriate amount depending on the use envisaged. It is preferably present in a concentration ranging from 0.01 to 20%, and better still from 0.5 to 10%, by weight relative to the total weight of the composition.

The composition of the invention can be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a two-phase product, a dispersion of oil in an aqueous phase using spherules, it being possible for these spherules to be polymer nanoparticles such as nanospheres and nanocapsules or alternatively lipid vesicles of ionic and/or nonionic type.

This composition can be more or less fluid and can have the appearance of a white or coloured cream, an ointment, a milk, a lotion, a serum, a paste or a mousse. It can optionally be applied to the skin in aerosol form. It can also be in solid form and, for example, in the form of a stick.

The composition according to the invention can comprise any adjuvant conventionally used in the cosmetics or dermatological field, in the usual concentrations. These adjuvants are chosen, in particular, from fatty substances, preserving agents, gelling agents, fragrances, emulsifiers and surfactants, water, antioxidants, fillers, solvents, fragances, active agents (hydrophilic or lypopyhilic) and screening agents, and mixtures thereof.

As fatty substances which can be used in the invention, mention may be made of mineral oils (liquid petroleum jelly), oils of plant origin (apricot oil), oils of animal origin, synthetic oils, silicone oils (cyclomethicone, phenyltrimethicone) and fluoro oils. Fatty alcohols, fatty acids, waxes and resins, and mixtures thereof, can also be used.

As emulsifiers which can be used in the invention, mention may be made, for example, of silicone-based emulsifiers such as dimethiconecopolyols and alkyldimethiconecopolyols. As dimethiconecopolyol, mention may be made of the mixture of dimethiconecopolyol and cyclomethicone sold under the name "Q2-3225C" by the company Dow Corning and the product sold under the name "SF-1228" by the company General Electric. As alkyldimethiconecopolyol, mention may be made of lauryldimethiconecopolyol such as, for example, the product sold under the name "Q2-5200" by the company Dow Corning, and cetyldimethiconecopolyol such as, for example, the product sold under the name "Abil EM 90" by the company Goldschmidt.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and as lipophilic gelling agents, mention may be made of modified clays such as bentones, metal salts of fatty acids, hydrophobic silica and polyethylenes.

As active agents, use may be made in particular of moisturizers such as polyols (glycerol, propylene glycol), vitamins, keratolytic agents and/or desquamating agents (salicylic acid and its derivatives, a-hydroxy acids), anti-inflammatory agents and calmants, and mixtures thereof. In the event of incompatibility, these active agents can be incorporated into spherules, in particular ionic or nonionic vesicles and/or nanoparticles (nanocapsules and/or nanospheres) in order to isolate them from each other in the composition.

As filler, the composition according to the invention can contain, for example, nylon and starch and its derivatives.

In addition, in order to further improve the stability of the composition containing ascorbic acid, the pH of the aqueous phase of the composition can be adjusted to a value ranging from 5.5 to 7.5, and in particular to pH 6. Any appropriate basic agent can be added to the composition in order to adjust the pH, this agent being chosen in particular from inorganic bases such as alkali-metal hydroxides (sodium hydroxide and potassium hydroxide) or ammonium hydroxides, and organic bases, in particular amphoteric bases, i.e. bases having both anionic and cationic functional groups.

The amphoteric bases can be primary, secondary, tertiary or cyclic organic amines and more especially amino acids. As examples of amphoteric bases, mention may be made of glycine, lysine, arginine, taurine, histidine, alanine, valine, cysteine, trihydroxymethylaminomethane (TRISTA) and triethanolamine.

The basic agent is used in an amount which is sufficient to bring the pH of the composition to between 5.5 and 7.5 and preferably to pH 6. This amount can range, for example, from 0.1 to 5% and preferably from 0.5 to 2% of the total weight of the emulsion.

A small amount of an acid, such as citric acid, can be added to the basic agent to allow a buffer effect to be obtained. This acid can be used, for example, in an amount ranging from 0.1 to 5% of the total weight of the composition.

The composition according to the invention can constitute, in particular, a cleansing, protective, treatment or care composition for facial skin and/or for the body, mucous membranes and/or keratin fibres, i.e. the hair and/or the eyelashes.

Thus, another subject of the invention is the cosmetic use of the composition according to the invention for cleansing and/or treating and/or protecting the skin and/or mucous membranes and/or keratin fibres.

The subject of the invention is also the use of the composition according to the invention for the preparation of a cream or ointment intended for the dermatological treatment of human skin.

The subject of the invention is also a cosmetic and/or dermatological process for treating the skin, mucous membranes and/or keratin fibres, characterized in that it consists in applying a composition as defined above to the skin, the mucous membranes and/or the keratin fibres.

Test

This test shows the stabilization of ascorbic acid by the system according to the invention. An aqueous solution of pH 6, containing 2% by weight of ascorbic acid, is prepared. The following are added to 10 ml of this solution:

Composition A (comparative example): 0.05% by weight of Dequest 2046

Composition B (comparative example): 0.05% by weight of sodium metabisulphite

Composition C (according to the invention): 0.05% by weight of Dequest 2046+0.05% of sodium metabisulphite.

The colour change (DOD) of these compositions, kept for 3 days at 45° C. in stoppered flasks, is evaluated by measuring the optical density at 405 nm, relative to the control solution containing neither Dequest 2046 nor metabisulphite. The results are collated in the table below.

| Composition | ΔOD |
| --- | --- |
| Composition A (comparative example) | −13.5% |
| Composition B (comparative example) | +76.06 |
| Composition C (according to the invention) | −38.54% |

This table shows a decrease in the colour change with composition A, an increase in the colour change with composition B and a marked decrease in the colour change with composition C according to the invention.

Consequently, a synergistic effect of the system according to the invention for stabilizing ascorbic acid is observed.

The examples below of compositions according to the invention are given by way of illustration and with no limiting nature. The amounts therein are given as a % by weight, except where otherwise mentioned.

EXAMPLE 1

Composition for a Radiant Complexion

| Phase A: | |
| --- | --- |
| - Mixture of dimethiconecopolyol and cyclomethicone (Q2-3225C from Dow Corning) | 20% |
| - Phenyltrimethicone (Dow Corning 556 Fluid) | 4% |
| - Apricot oil | 3% |
| Phase B: | |
| - Nylon | 125% |
| Phase C: | |
| - Glycerol | 23% |
| - Vitamin C | 5% |
| - Sodium metabisulphite | 0.05% |
| - Dequest 2041 | 0.05% |
| - Galactose | 0.33% |
| - Glucose | 0.33% |
| - Mannose | 0.33% |
| - Propylene glycol | 6% |
| - Sodium hydroxide | 1.93% |
| - Citric acid | 1.24% |
| - Preserving agent | 0.2% |
| - Demineralized water | q.s. 100% |

Procedure: The aqueous phase is prepared at room temperature; the oily phase is also prepared at room temperature and the nylon is added thereto. Next, the aqueous phase is poured slowly into the oily phase with rapid stirring.

A white water-in-oil emulsion is obtained, which is capable of enhancing the radiance of the skin's complexion and of smoothing out lines on the face.

The French priority document No. 97 10903 is incorporated herein by reference.

What is claimed is:

1. A composition for stabilizing ascorbic acid, comprising at least one phosphonic acid derivative selected from the group consisting of ethylenediaminetetra (methylenephosphonic acid), hexamethylenediaminetetra (methylene phosphonic acid), diethylenetriaminepenta (methylenephosphonic acid), and salts thereof and at least one metabisulphite, said phosphonic acid derivative and said metabisulphite being present in sufficient amounts to act in synergy.

2. The composition of claim 1, wherein the weight ratio between the metabisulphite and the phosphonic acid derivative is from 1 to 5.

3. The composition of claim 1, wherein the phosphonic acid derivative is ethylenediaminetetra (methylenephosphonic acid).

4. The composition of claim 1, wherein the phosphonic acid derivative is the sodium salt of ethylenediaminetetra (methylenephosphonic acid).

5. The composition of claim 1, wherein the metabisulphite is selected from the group consisting of alkali-metal, alkaline-earth metal and ammonium salts of anhydrosulphurous acid, and mixtures thereof.

6. The composition of claim 1, wherein the metabisulphite is sodium metabisulphite.

7. The composition of claim 1, which is a composition for topical application.

8. The composition of claim 1 which contains from 0.005 to 5% by weight of the phosphonic acid derivative relative to the total weight of the composition.

9. The composition of claim 1 which contains from 0.005 to 5% by weight of the metabisulphite relative to the total weight of the composition.

10. The composition of claim 1 which contains from 0.01 to 20% by weight of ascorbic acid relative to the total weight of the composition.

11. The composition of claim 1 which contains an aqueous phase with a pH ranging from 5.5 to 7.5.

12. The composition of claim 11 in which the pH of the aqueous phase is adjusted using a basic agent chosen from inorganic bases and organic bases.

13. The composition of claim 1 which contains an aqueous phase of pH 6.

14. The composition of claim 1 further comprising at least one adjuvant chosen from water, fatty substances, preserving agents, gelling agents, surfactants and emulsifiers, antioxidants, fillers, solvents, fragrances, dyestuffs, screening agents and active agents, and mixtures thereof.

15. Cosmetic process for treating skin, mucous membranes or keratin fibres, comprising: applying a composition of claim 1 to human skin, mucous membranes or keratin fibres.

16. A method of stabilizing ascorbic acid, comprising adding synergistic amounts of a phosphonic acid derivative selected from the group consisting of ethylenediaminetetra (methylenephosphonic acid), hexamethylenediaminetetra (methylene phosphonic acid), diethylenetriaminepenta (methylenephosphonic acid), and salts thereof and a metabisulphite.

17. The method of claim 16, wherein the weight ratio between the metabisulphite and the phosphonic acid derivative is from 1 to 5.

18. The method of claim 16, wherein the phosphonic acid derivative is ethylenediaminetetra(methylenephosphonic acid).

19. The method of claim 16, wherein the phosphonic acid derivative is the sodium salt of ethylenediaminetetra (methylenephosphonic acid).

20. The method of claim 16, wherein the metabisulphite is sodium metabisulphite.

* * * * *